(12) United States Patent  (10) Patent No.: US 7,513,722 B2
Greenberg et al.  (45) Date of Patent: Apr. 7, 2009

(54) COLLET COLLAR STOP FOR A DRILL BIT

(75) Inventors: Alex M. Greenberg, New York, NY (US); Paul Mulhauser, New York, NY (US); Karl Dallas Kirk, III, New York, NY (US)

(73) Assignee: Greenberg Surgical Technologies, LLC, New York, NY (US)

( * ) Notice: Subject to any disclaimer, the term of this patent is extended or adjusted under 35 U.S.C. 154(b) by 259 days.

(21) Appl. No.: 11/157,882

(22) Filed: Jun. 21, 2005

(65) Prior Publication Data

US 2006/0008332 A1  Jan. 12, 2006

Related U.S. Application Data

(63) Continuation-in-part of application No. 10/748,338, filed on Dec. 30, 2003, now Pat. No. 7,210,881.

(51) Int. Cl.
*B23B 49/00* (2006.01)
(52) U.S. Cl. .......................................... 408/202; 433/75
(58) Field of Classification Search ................ 408/202, 408/241 S, 14, 110, 113; 433/75, 165; 606/80
See application file for complete search history.

(56) References Cited

U.S. PATENT DOCUMENTS

| | | | | |
|---|---|---|---|---|
| 264,791 A | * | 9/1882 | Sutton | 408/192 |
| 460,639 A | * | 10/1891 | Holt | 408/230 |
| 679,693 A | * | 7/1901 | Burkhart | 408/191 |
| 1,105,154 A | * | 7/1914 | McMillen | 408/202 |
| 1,267,704 A | * | 5/1918 | Skrukrud | 408/191 |
| 1,961,604 A | * | 6/1934 | Broemme et al. | 82/1.4 |
| 2,477,891 A | * | 8/1949 | O'Neill | 408/113 |
| 2,823,563 A | * | 2/1958 | Nipken | 408/110 |
| 2,915,925 A | * | 12/1959 | Nipken | 408/113 |
| 3,620,637 A | * | 11/1971 | Brown | 408/202 |
| 4,019,827 A | * | 4/1977 | Christianson et al. | 408/202 |
| 4,335,295 A | * | 6/1982 | Fowler | 219/121.85 |
| 5,382,250 A | * | 1/1995 | Kraus | 606/80 |
| 5,795,110 A | * | 8/1998 | Wirth et al. | 408/110 |
| 5,882,151 A | * | 3/1999 | Wirth et al. | 408/110 |
| 6,716,215 B1 | * | 4/2004 | David et al. | 606/80 |
| 7,048,477 B2 | * | 5/2006 | Abrams | 408/1 R |

FOREIGN PATENT DOCUMENTS

DE  2402516  *  7/1975
JP  52044489 A  *  4/1977

* cited by examiner

*Primary Examiner*—Daniel W Howell
(74) *Attorney, Agent, or Firm*—Cohen Pontani Lieberman & Pavane LLP (57) ABSTRACT

A stop for a drill bit having a shaft, the stop having a first member which includes a collet. The collet is configured to receive the shaft of the drill bit and is positionable along the shaft of the drill bit. The stop also has a second member which includes a clamp, for clamping the first member in a desired position along the shaft of the drill bit by securing the collet in a desired position along the shaft of the drill bit. The stop further has an abutment surface on one of the first and second members, for limiting the depth of penetration of the drill bit into an object, the abutment surface being disposed in a fixed position along the shaft of the drill bit by the clamping of the first and second members.

29 Claims, 6 Drawing Sheets

COLLET COLLAR STOP FOR A DRILL BIT

CROSS REFERENCE TO RELATED APPLICATIONS

This application is a continuation-in-part of application Ser. No. 10/748,338, filed Dec. 30, 2003, now issued on May 1, 2007 as U.S. Pat. No. 7,210,881, the disclosure of which is hereby incorporated by reference.

BACKGROUND OF THE INVENTION

1. Field of the Invention

This invention is directed to the field of hardware for use with drills, and, more particularly, to a collet collar stop for a drill bit which utilizes two molded pieces to attach to the drill bit and prevent the user from drilling too deeply into a surface by limiting the depth of penetration of the drill bit into the surface.

2. Description of the Related Art

Drills are common hand tools. They are used in many applications, from home repair to surgery. One common problem associated with the use of drills is that it may be difficult to identify the desired depth of a hole being drilled into a surface. In some applications, such as installing door hinges, attaching legs to a table, or during surgery (e.g., dental surgery, neurosurgery, orthopedic surgery, or maxillofacial surgery), drilling the hole to a precise depth is of crucial importance, and so precise control of the depth of penetration of the drill bit into the surface is essential.

In simple applications, crude means have existed for providing a stop for the drill bit. In carpentry, for example, it is common to provide a visual stop for a drill bit by applying a long piece of masking tape to the exterior of the bit itself, whereby the edge of the tape closest to the tip of the drill is aligned with the desired maximum depth of penetration of the bit. The tape can also be wrapped about the bit several times to establish a shoulder which abuts the surface into which the drill penetrates. This functions to limit the travel of the bit beyond the desired depth. While this approach works satisfactorily in carpentry, it is not appropriate, for example, in oral surgery, where a more precise (and sanitary) form of stop is needed. It also is difficult to re-position for subsequent uses.

The prior art includes many known stops for drill bits. However, prior art drill bits may be difficult to implement, either because they require complicated manipulation or because they require the use of special types of drill bits to accommodate the stop. Additionally, many prior art drill bits were specially adapted for use with drill bits of a single size, and could not readily be used on standard drill bits having shafts of varying diameters. Thus, it would be useful to have a stop for a drill bit that could be used with standard drill bits, and it would be particularly useful to have a single stop which could be used with standard drill bits having a range of diameters.

It would also be useful to have a kit which includes a plurality of stops for drill bits, with each stop being individually useful with standard drill bits having a range of diameters.

Accordingly, there is a need in the art for a drill bit stop which provides means for reliably and precisely setting the depth of penetration of a drill bit with a simple attachment arrangement, and which may be used with drill bits having a varying range of diameters.

SUMMARY OF THE INVENTION

In accordance with a preferred embodiment of the invention, there is provided a stop for a drill bit having a shaft, the stop having a first member which includes a collet. The collet is configured to receive the shaft of the drill bit and is positionable along the shaft of the drill bit. The stop also has a second member which includes a clamp, for securing the first member in a desired position along the shaft of the drill bit. The stop has an abutment surface on one of the first and second members, for limiting the depth of penetration of the drill bit into the surface of an object, the abutment surface being disposed in a fixed position along the shaft of the drill bit by the locking of the first and second members.

In different embodiments of the invention, the collet may include a plurality of fingers which together grasp the shaft of the drill bit, and thereby accommodate drill bits having a range of diameters, and the second member includes a tapered cone which fits over the collet, to cause the fingers of the collet to grip the shaft of the drill bit and hold the stop in place to resist movement thereof when in use.

In another embodiment of the invention, a kit has a plurality of drill bit stops which each accommodate a different range of drill bit diameters, and which together may accommodate a set of drill bits having different diameters such as may be found in a common set of drill bits.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, are merely intended to conceptually illustrate the structures and procedures described herein.

BRIEF DESCRIPTION OF THE DRAWINGS

In the drawings.

The foregoing and other advantages and features of the invention will become more apparent from the detailed description of the preferred embodiments of the invention given below with reference to the accompanying drawings in which like reference numerals refer to similar elements.

DETAILED DESCRIPTION OF THE PRESENTLY PREFERRED EMBODIMENTS

Figure 1:
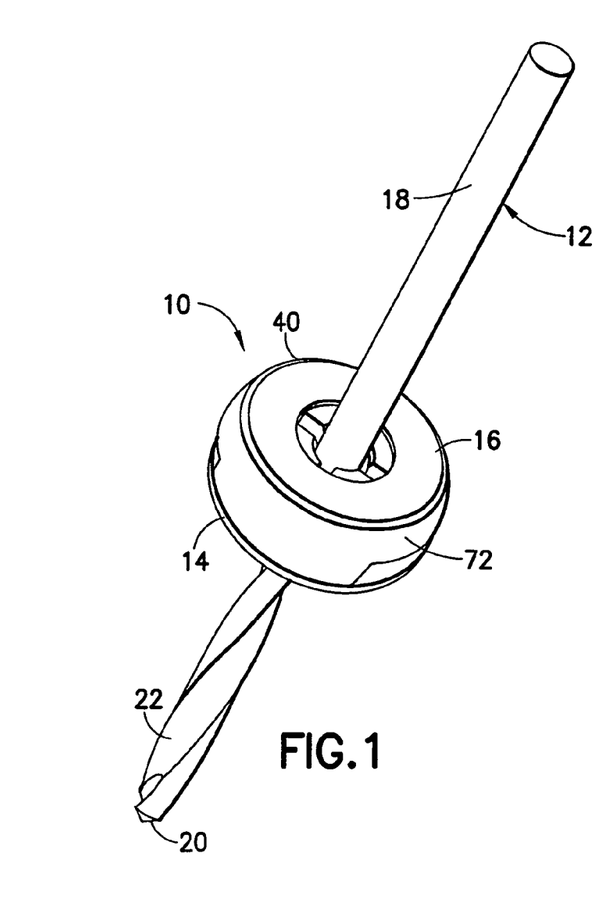
FIG. 1 is a perspective of a stop in accordance with the invention, as shown in use with a standard drill bit.

FIG. 1 shows, generally at 10, a stop for a drill bit 12 in accordance with the invention. Stop 10 includes a first member 14 and a second member 16. Drill bit 12 includes a shaft 18, a cutting point 20 and at least one groove 22.

Figure 2:
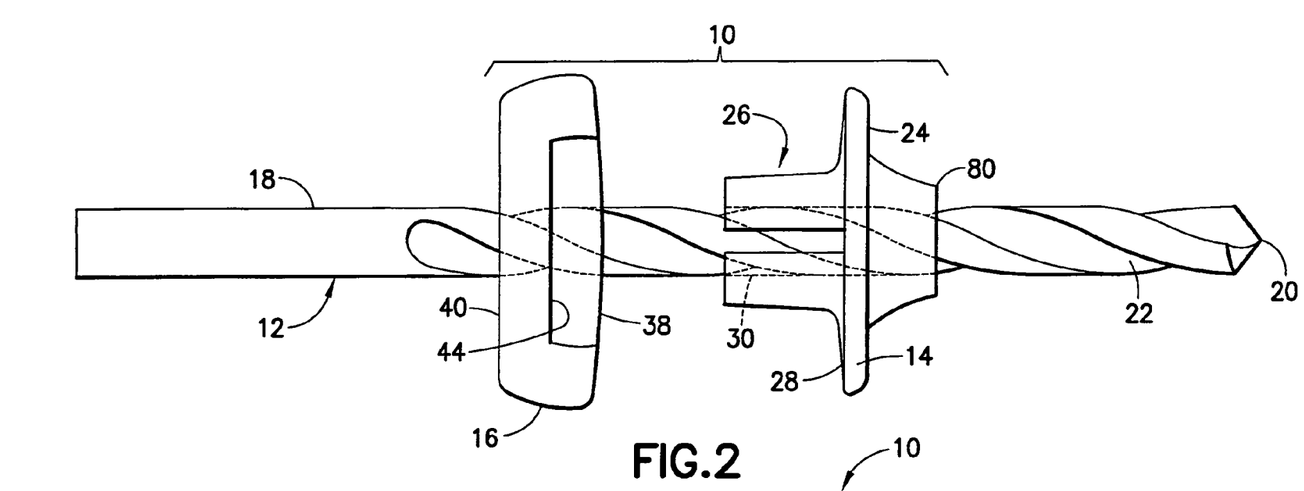
FIG. 2 is a side exploded elevation of the stop/drill bit arrangement of FIG. 1, with the components of the stop disassembled.
Figure 3:
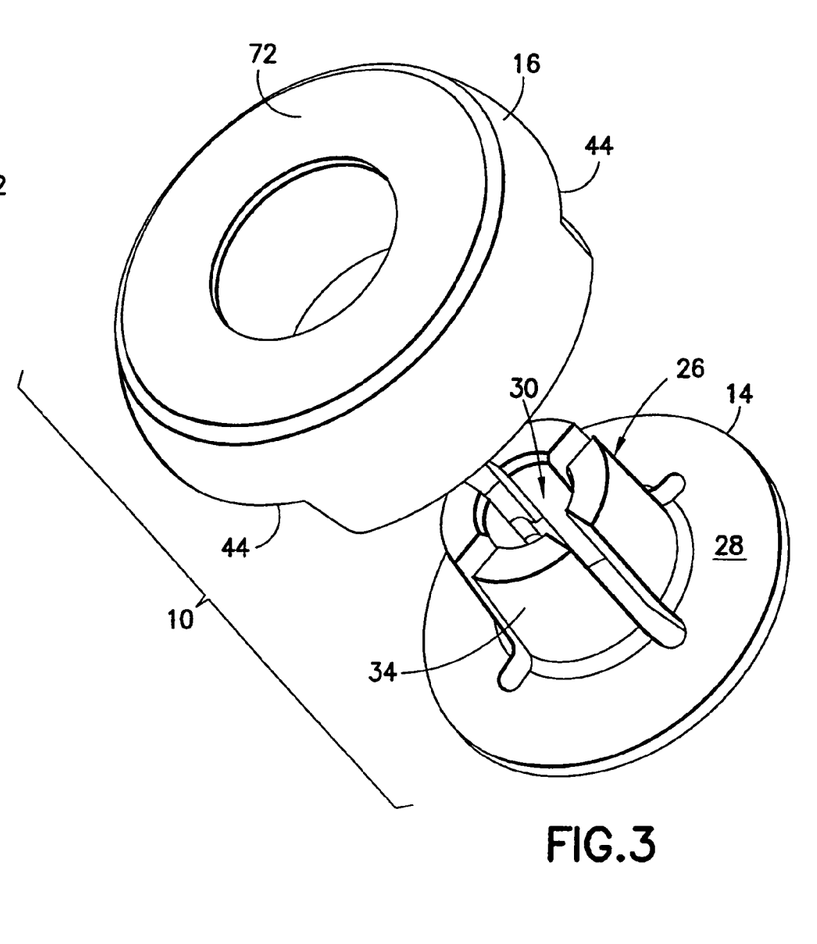
FIG. 3 is an exploded perspective of the stop of FIGS. 1 and 2.

As shown more clearly in FIGS. 2 and 3, first member 14 includes a generally planar abutment surface 24 on one side thereof and a collet 26 projecting from a rigid rear surface 28 thereof. In a preferred embodiment, rear surface 28 has a generally flat outer rim (see FIG. 3). Collet 26 includes an aperture 30 which is configured to receive shaft 18 of drill bit 12 therein. In a preferred embodiment of the invention, collet 26 includes a plurality of bendable finger elements 32 biased inwardly toward shaft 18, and collectively having an outer surface 34. More preferably at least three, and most preferably four, finger elements 32 together define a generally frusto-conical shape with the smaller end of the frustum positioned farthest from rear surface 28 as shown in FIG. 3. Finger elements 32 are therefore positioned on first member 14 opposite abutment surface 24, and are biased inwardly towards the center of aperture 30 to grip shaft 18 of drill bit 12. Alternately, collet 26 may be made of a deformable elastomeric material which stretches to accommodate drill bits having diameters which fall in a predetermined range, and which resiliently grips shaft 18 of drill bit 12.

Preferably, first and second members 14 and 16 are injection molded of a soft plastic, so that when abutment surface 24 abuts the surface into which drill bit 12 is drilling, it does not mar that surface. Suitable materials include any non-rigid, complaint plastic material, such as nylon.

Figures 4, 6, 7:
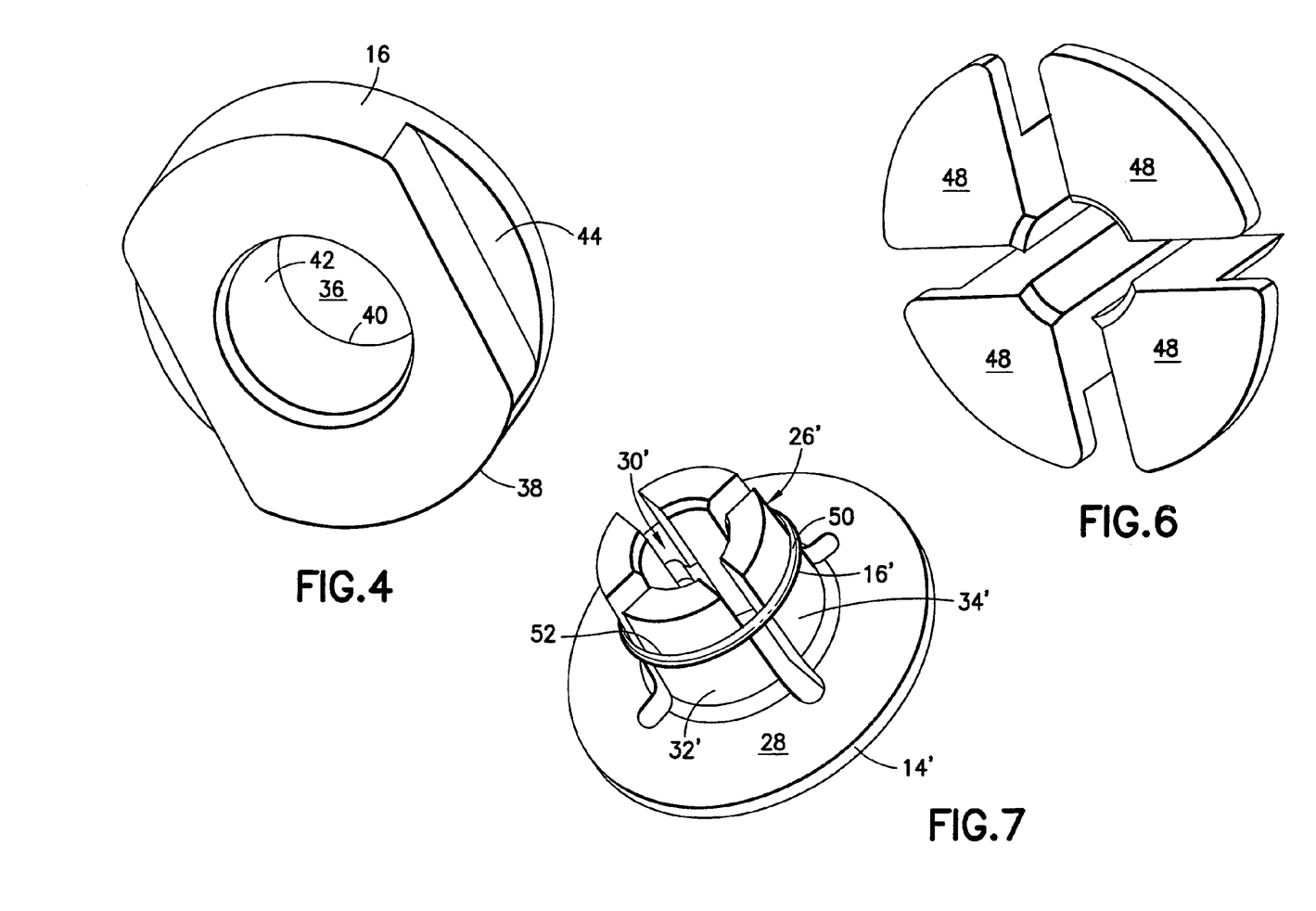
FIG. 4 is a bottom perspective of one member of the stop of FIG. 3.
FIG. 6 is a bottom perspective of an alternate embodiment of one member of the inventive stop.
FIG. 7 is a perspective of a further alternate embodiment of the inventive stop.

As best shown in FIG. 4, second member 16 includes a central opening 36 which is tapered from a first surface 38 to a second surface 40 thereby forming a tapered conical portion 42 which is dimensioned to receive finger elements 32 of collet 26, and a recessed rigid surface 44 disposed opposite rear surface 28. Preferably, when first and second members 14 and 16 are assembled (FIG. 5), rigid surface 44 and rear surface 28 are spaced apart by a distance sufficient to permit the insertion therebetween of an implement, such as a screwdriver.

As explained above, stop 10 may be used to provide a means for limiting the depth of penetration of drill bit 12 into an object. This is accomplished by the user first determining the depth to which drilling is desired, i.e., the length of shaft 18 corresponding to the desired depth of the hole to be drilled in the object, measured from cutting point 20. The user then positions first member 14 along shaft 18 of drill bit 12 so that abutment surface 24 is disposed at that position along the length of shaft 18 which corresponds to the desired depth of drilling. Finger elements 32 clamp shaft 18 and hold first member 14 in position, but not sufficiently tightly such that first member 14 may yet act as a stop. This requires that first member 14 be secured in place. In the preferred embodiment, the securing function is accomplished by placing shaft 18 within the tapered conical portion 42, and sliding second member 16 along shaft 18 until finger elements 32 are received in central opening 36. Tapered conical portion 42 serves as a guide for finger elements 32. As second member 16 slides over finger elements 32, tapered conical portion 42 causes finger elements 32 to clamp against shaft 18, thereby securing stop 10 in its desired position. This clamping action allows collet 26 to maintain abutment surface 24 in the desired relation to cutting point 20 to limit the depth of penetration of drill bit 12 into the surface, and may secure stop 10 in position during the normal use of drill bit 12 to drill into a surface. The clamping action may be released by prying apart first member 14 from second member 16 such as, for example, by placing a screwdriver between surfaces 28 and 42, and twisting, thereby imparting relative opposed forces to these two surfaces, loosening the clamping action and permitting the removal of stop 10 from drill bit 12.

In one embodiment, rigid surface 44 comprises a "cut out" portion of the exterior of second member 16. This cut out portion provides a clearance between surfaces 28 and 38 to facilitate the separation of members 14 and 16.

Other embodiments with other features of the invention are possible, as well.

Figure 5:
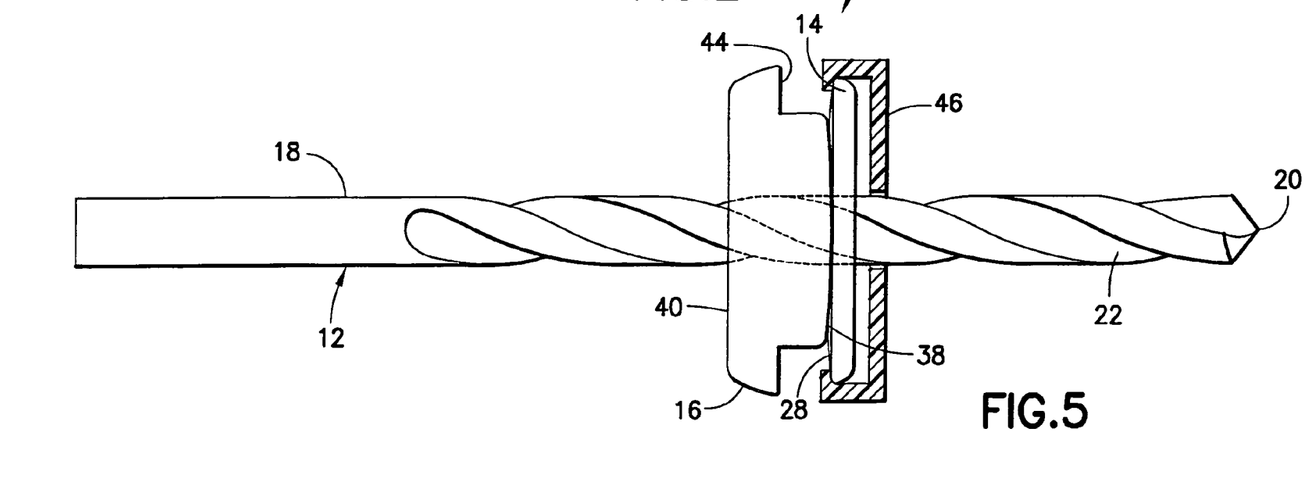
FIG. 5 is an elevation of an alternate embodiment of the inventive stop.

For example, as shown in FIG. 5, a rotatable abutment 46 may be rotatably mounted on first member 14, so that, when stop 10 contacts the surface into which drilling is desired, rotatable abutment 46 does not rotate relative to the surface, and instead rotates relative to the turning of drill bit 12, to avoid marring the surface. In the illustrated embodiment, this is accomplished by the simple expedient of forming or otherwise attaching rotatable abutment 46 onto the bottom of first member 14, although other means, such as mounting abutment surface 46 to first member 14 via bearings, or a tongue-and-groove arrangement or the like may be used.

In another embodiment of the invention, shown in FIG. 6, several discontiguous pieces 48 form an abutment surface having discontiguous points of contact with the surface into which the user the wishes to drill, which points of contact together define a plane, or some other surface (regular or irregular) intended to conform to the surface into which drill bit 12 drills.

In a further alternative embodiment shown in FIG. 7, second member 16' may comprise a resilient locking ring 50 positioned in a groove 52 on finger elements 32' of collet 26', or other locking means to snap fit over collet 26', and lock collet 26' over the shaft of the drill bit. For example, locking ring 50 may be "C" shaped, and include teeth at opposed ends thereof for engaging at least two of a plurality of notches in groove 52 in a ratchet-type arrangement. Locking ring 50 may be made of any suitable resilient material, such as plastic or spring metal. A single locking ring 50 may accommodate collets of different sizes, depending upon the strength of the resiliency of the locking ring and the clamping force desired to be exerted on shaft 18. Additionally, the thickness of finger elements 32' of a collet may be adjusted so that outer surface 34' is substantially the same diameter at equivalent points on several collets, or at different points on different collets, so that a single locking ring may secure more than one collet.

Figure 8:
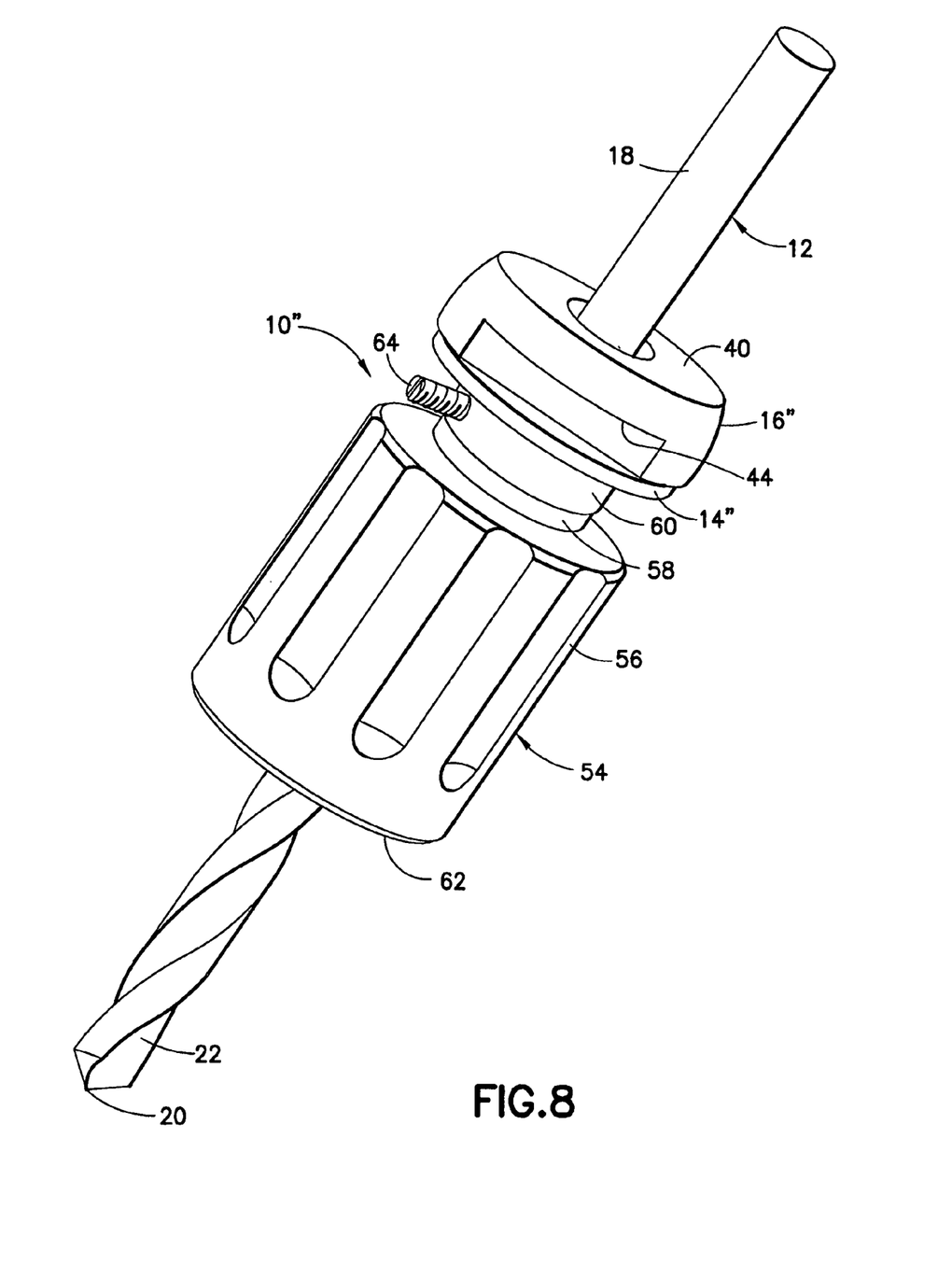
FIG. 8 is a perspective of yet another alternate embodiment of the inventive stop, in which the stop includes both fine and coarse adjustment means.

A still further embodiment of the invention is shown in FIG. 8, in which a stop 10" for use with a drill bit 12 includes a first member 14" and a second member 16" which are generally similar to first and second members 14 and 16 shown in FIGS. 1-4. The difference resides in the provision of a fine adjustment means 54 attached to first member 14". It will be appreciated, however, that fine adjustment means 54 can be, alternatively, attached to second member 16".

In certain applications, it is imperative that the depth of the stop be controlled to a very fine degree. In such applications, the relatively coarse adjustment provided by the clamping of stop 10 to shaft 18 may be inadequate. To meet the needs of such applications, first and second members 14" and 16" of stop 10" act as a coarse adjustment means (such as broadly described in application Ser. No. 10/748,338, filed Dec. 30, 2003, now issued on May 1, 2007 as U.S. Pat. No. 7,210,881. The nature of the clamping arrangement of the preferred embodiment makes it possible that stop 10" may shift slightly when being locked in place. While, for most applications, this slight shift is irrelevant, for those applications where the shift matters, a fine adjustment means 54 may be used.

Fine adjustment means 54 preferably comprises a rotatable body 56 which includes a threaded portion 58 mounted to a complementary threaded portion 60 within first member 14". Rotatable body 56 further includes an abutment surface 62 which may be positioned at a desired depth relative to the surface into which drill bit 12 is intended to drill.

Once stop 10" is positioned generally so that abutment surface 62 is approximately in its desired position, it may be adjusted by rotating rotatable body 56 along threaded portions 58 and 60 to the precisely desired position. It is preferred that threaded portions 58 and 60 be angled so that they do not tend to rotate once abutment surface 62 contacts the surface. A left-hand thread will accomplish this objective in a standard electric drill, which uses a right-hand rotation. It is also possible to lock fine adjustment means 54 in position, such as via a set screw 64 which may be positioned on first member 14, second member 16 (as shown) or on fine adjustment means 54.

Figure 9:
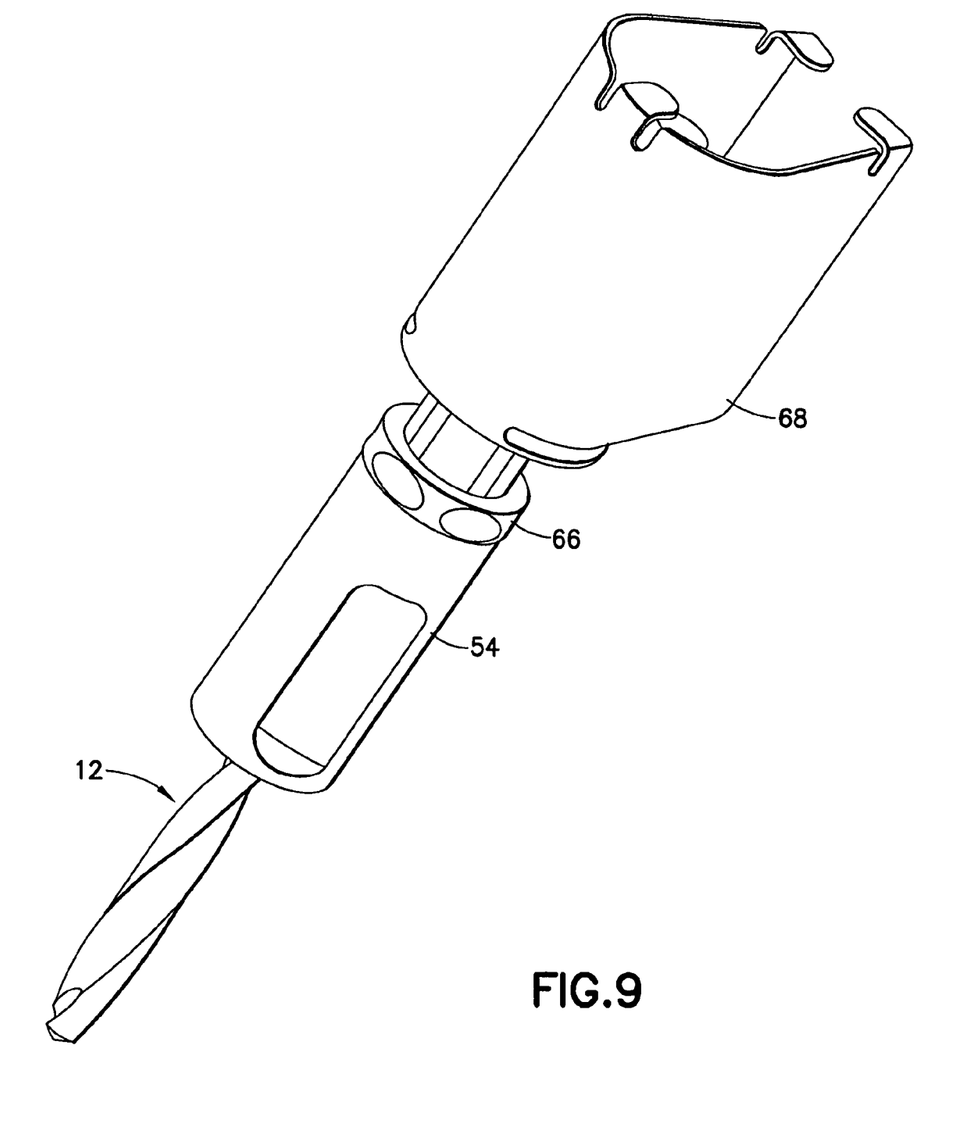
FIG. 9 is a perspective of a still further embodiment of the inventive stop, with an alternate means for securing the relative positions of the fine and coarse adjustment means.

Alternatively, a jam nut 66 may be used (FIG. 9) to secure the relative position of fine and coarse adjustment means 54, 68, respectively, on bit 12.

It is noted that threaded portion 60 may be located on either the top of rotatable body 56 or on the bottom of first element 14". It is preferred, however, that the threads on first member 14" be located within stop 10", so that stop 10" may be used without fine adjustment means 54 if desired.

Figure 10:
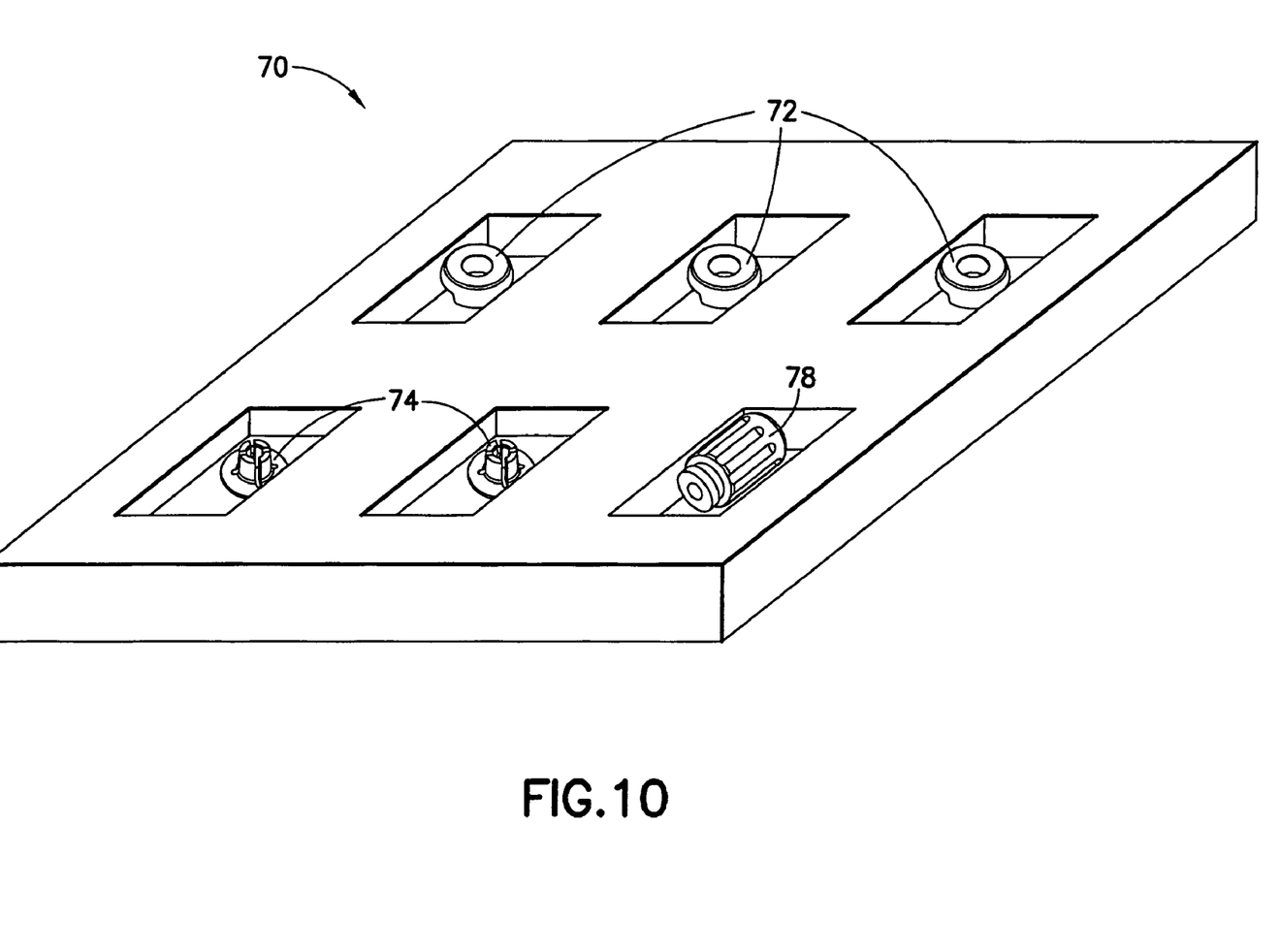
FIG. 10 is a perspective of a kit of a plurality of different stops according to the preferred embodiment of the invention, and including a single fine adjustment means, such as shown in FIG. 8.

It will also be appreciated by those of ordinary skill in the art that a plurality of similar stops designed to accommodate different ranges of diameters of drill bits could be employed together as a kit, so that a few stops could be used to accommodate a wide range of drill bit diameters, such as one might find in a standard set of drill bits. Such a kit is shown in FIG. 10, generally at 70, and comprises a plurality of collets 72 and locking members 74. If a plurality of stops are used in a kit, it is preferred that each includes indicia 76 indicating the range of drill bit diameters with which it may be used, as is shown in FIGS. 1 and 3. It is also possible, depending upon the configuration of collets 72 used in kit 70 that a single clamping (second) member 74 may accommodate more that one collet 72, so that kit 70 may require fewer locking members 74 than collets 72. Kit 70 may also include a fine adjustment means 78.

In another embodiment of the invention, drill stop 24 may include a countersink 80 (FIG. 2) to permit creation of a countersink on the surface into which drill bit 12 drills, in known fashion.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

By way of example, collet 26 may be segmented, with separate sections thereof being independently movable, with a locking means, such as a notch, therein for locking collet 26 and second member 16 together.

What is claimed is:

1. A stop for a drill bit having a shaft defining an axis, said stop comprising:
   a first member including
      a rear surface extending radially away from the axis of the drill bit, and
      a collet,
         said collet being configured to receive said shaft of said drill bit,
         said collet being positionable along said shaft of said drill bit,
         said collet being capable of receiving shafts having a range of diameters, and
         said collet including a plurality of flexible fingers,
            said fingers being deformably mounted to said rear surface, and
            said fingers being separated from one another by at least one generally "L"-shaped slot, said at least one slot extending radially inward from between said fingers into said rear surface of said first member;
   a second member including a clamp, for clamping said first member in a desired position along said shaft of said drill bit by releasably securing said collet in a desired position along said shaft of said drill bit; and
   an abutment on one of said first and second members, for limiting the depth of penetration of said drill bit into an object, said abutment being releasably securable in a fixed position along said shaft of said drill bit by said locking of said first and second members.

2. The stop of claim 1, wherein said collet has a generally frusto-conical shape, and said clamp includes a mating portion to engage said frusto-conical shape and thereby secure said stop in a desired position along said shaft of said drill bit.

3. The stop of claim 1, wherein said clamp includes a snap-fit arrangement.

4. The stop of claim 1, wherein said clamp includes a locking ring.

5. The stop of claim 1, wherein said abutment is generally planar.

6. The stop of claim 1, further including means for rotatably mounting said abutment with respect to said first member.

7. The stop of claim 1, wherein said clamp includes an unlocking means.

8. The stop of claim 7, wherein said first member includes a first rigid surface, and said unlocking means includes a second rigid surface, said second rigid surface being positioned in opposed relationship to said first rigid surface;
   whereby said first and second members may be separated by means of relative opposite pressure being exerted on said first and second rigid surfaces.

9. The stop of claim 8, wherein said relative opposite pressure may be excited by an implement; and said first and second rigid surfaces are spaced apart by a distance sufficient to permit the entry of said implement between said first and second rigid surfaces.

10. The stop of claim 1, further comprising a fine adjustment means;
  wherein said abutment is affixed to said fine adjustment means; and
  wherein said fine adjustment means is movably mounted to said one of said first and second members.

11. The stop of claim 10, wherein said fine adjustment means includes means for preventing unwanted movement of said fine adjustment means.

12. The stop of claim 11 wherein said means for preventing unwanted movement includes first threading on said one of said first and second members, and complementary second threading on said fine adjustment means, said first threading and said complementary second threading each being angled opposite to the direction of rotation of said drill bit, whereby abutment of said abutment against said object does not permit rotation of said fine adjustment means along said threading on said one of said first and second members.

13. The stop of claim 11 further comprising means for locking said fine adjustment means in a desired position along said shaft of said drill bit.

14. A kit comprising a first plurality of stops for a second plurality of drill bits, each of said second plurality of drill bits having a shaft with a diameter, the shaft defining an axis of the drill bit, said kit comprising:
  a third plurality of collets, each of said collets being configured to receive a shaft of at least one of said second plurality of drill bits having a diameter falling within a predetermined range of diameters and being positionable along said shaft of said at least one of stud second plurality of drill bits;
    each of said collets having a rear surface and, a plurality of fingers resiliently mounted to said rear surface, each of said fingers being separated from an adjacent one of said fingers by a generally "L"-shaped slot that extends into said rear surface;
  at least one clamp, each of said clamps being capable of securing at least one of said third plurality of collets in a desired position along a shaft of at least one of said second plurality of drill bits by releasably securing said at least one of said third plurality of said collets in a desired position along said shaft of said at least one of said second plurality of drill bits; and
  an abutment on one of said at least one of said third plurality of collets and said at least one clamp, for limiting the depth of penetration of said at least one drill bit into a surface, said abutment being disposed in a releasably fixed position along said shaft of said drill bit by said clamping of said least one of said third plurality of collets and said at least one clamp.

15. The kit of claim 14, wherein at least one of paid first plurality of stops includes indicia thereon for identifying a diameter of a drill bit shaft received therein.

16. The kit of claim 15, wherein said indicia identifies a range of diameters of drill bit shafts which may be received in said at least one of said first plurality of stops.

17. The kit of claim 14, further comprising indicia on one of said at least one collet and said at least one clamp for identifying the range of drill bit shaft diameters received therein.

18. The stop of claim 14, wherein at least one collet has a generally frusto-conical shape, and said at least one clamp includes a mating portion to engage said frusto-conical shape of said at least one collet and thereby secure said at least one collet in a desired position along said shaft of the drill bit with which it is being used.

19. The kit of claim 14, wherein said at least one clamp includes a snap-fit arrangement.

20. The kit of claim 14, wherein at least one of said at least one clamps is configured to be capable of securing at least two different ones of said third plurality of collets in place on a drill bit when in use.

21. The kit of claim 14, wherein said abutment is generally planar.

22. The kit of claim 14 wherein said at least one clamp includes an unlocking means.

23. The kit of claim 22, wherein at least one of said third plurality of collets includes a first rigid surface, and said unlocking means includes a second rigid surface, said second rigid surface being positioned in opposed relationship to said first rigid surface;
  whereby said at least one of said third plurality of collets and said at least one clamp may be separated by means of relative opposite pressure being exerted on said first and second rigid surfaces.

24. The kit of claim 23, wherein said relative opposite pressure may be exerted by an implement, and said first and second rigid surfaces are spaced apart by a distance sufficient to permit the entry of said implement between said first and second rigid surfaces.

25. The kit of claim 14, further comprising a fine adjustment means; and
  wherein said abutment is affixed to said fine adjustment means; and
  wherein said fine adjustment means is movably mounted to one of said third plurality of said collets and said at least one clamp.

26. The stop of claim 25, wherein said fine adjustment means includes means for preventing unwanted movement of said fine adjustment means along said shaft of said drill bit.

27. The stop of claim 26, wherein said means for preventing unwanted movement includes first threading on said one of said collets and said at least one clamp, and complementary second threading on said fine adjustment means, said first threading and said complementary second threading each being angled opposite to the direction of rotation of said drill bit, whereby abutment of said abutment against said object does not permit rotation of said fine adjustment means along said first threading and said complementary second threading.

28. The kit of claim 25 further comprising means for securing said fine adjustment means in a desired position along said shaft of said drill bit.

29. The kit of claim 26, wherein said securing means includes a set screw.

* * * * *